(12) United States Patent
Morton

(10) Patent No.: US 8,292,966 B2
(45) Date of Patent: Oct. 23, 2012

(54) ARTIFICIAL TOE JOINT

(75) Inventor: Troy N. Morton, Red Springs, NC (US)

(73) Assignee: Morton Ballard Arthrotechnology, LLC., Cedar Hills, UT (US)

( * ) Notice: Subject to any disclaimer, the term of this patent is extended or adjusted under 35 U.S.C. 154(b) by 567 days.

(21) Appl. No.: 12/027,590

(22) Filed: Feb. 7, 2008

(65) Prior Publication Data
US 2008/0195215 A1 Aug. 14, 2008

Related U.S. Application Data

(60) Provisional application No. 60/889,195, filed on Feb. 9, 2007.

(51) Int. Cl.
*A61F 2/42* (2006.01)
(52) U.S. Cl. .................................. 623/21.19
(58) Field of Classification Search ..... 623/21.15–21.19
See application file for complete search history.

(56) References Cited

U.S. PATENT DOCUMENTS

| | | | |
|---|---|---|---|
| 4,232,404 A * | 11/1980 | Samuelson et al. | 623/21.18 |
| 4,257,129 A | 3/1981 | Volz | |
| 4,328,593 A | 5/1982 | Sutter et al. | |
| 4,356,572 A | 11/1982 | Guillemin et al. | |
| 4,642,122 A | 2/1987 | Steffee | |
| 4,725,280 A | 2/1988 | Laure | |
| 4,787,908 A * | 11/1988 | Wyss et al. | 623/21.15 |
| 5,037,440 A | 8/1991 | Koenig | |
| 5,047,059 A * | 9/1991 | Saffar | 623/21.15 |
| 5,067,964 A | 11/1991 | Richmond et al. | |
| 5,147,386 A | 9/1992 | Carignan et al. | |
| 5,222,984 A | 6/1993 | Forte | |
| 5,263,987 A | 11/1993 | Shah | |
| 5,425,777 A | 6/1995 | Sarkisian et al. | |
| 5,458,648 A * | 10/1995 | Berman et al. | 623/21.19 |
| 5,549,690 A * | 8/1996 | Hollister et al. | 623/21.15 |
| 5,702,472 A | 12/1997 | Huebner | |
| 5,728,163 A | 3/1998 | Maksene | |
| 6,409,767 B1 * | 6/2002 | Perice et al. | 623/21.18 |
| 6,540,786 B2 | 4/2003 | Chibrac et al. | |
| 6,652,587 B2 | 11/2003 | Felt et al. | |
| 6,663,669 B1 * | 12/2003 | Reiley | 623/21.18 |
| 6,926,739 B1 * | 8/2005 | O'Connor et al. | 623/21.18 |
| 6,942,475 B2 | 9/2005 | Ensign et al. | |
| 2004/0236429 A1 | 11/2004 | Ensign et al. | |
| 2005/0010299 A1 | 1/2005 | Disilvestro | |
| 2005/0049710 A1 | 3/2005 | O'Driscoll et al. | |
| 2005/0102032 A1 | 5/2005 | Beynnon et al. | |
| 2005/0143818 A1 | 6/2005 | Yuan et al. | |
| 2005/0216090 A1 | 9/2005 | O'Driscoll et al. | |
| 2005/0267584 A1 | 12/2005 | Burdulis, Jr. et al. | |
| 2006/0074492 A1 | 4/2006 | Frey | |
| 2006/0149261 A1 | 7/2006 | Nilsson et al. | |

OTHER PUBLICATIONS

Authorized officer: Thomas Dunn, International Preliminary Report (Aug. 6, 2009) on Patentability for International Application No. PCT/US2008/053495 filed Feb. 8, 2008.
International Search Report re: International application No. PCT/US08/53495, Aug. 15, 2008.

* cited by examiner

*Primary Examiner* — Thomas J Sweet
*Assistant Examiner* — Ann Schillinger
(74) *Attorney, Agent, or Firm* — Bateman IP

(57) ABSTRACT

An artificial toe joint utilizes a ball in socket joint structure and arms or side walls which are exterior to the bone. The resulting joint provides improved strength and durability, and may be used to repair joints which are not suitable for installation of a prior art artificial joint.

24 Claims, 7 Drawing Sheets

ARTIFICIAL TOE JOINT

RELATED APPLICATIONS

The application claims the benefit of U.S. Provisional Patent Application Ser. No. 60/889,195, filed Feb. 9, 2007, which is incorporated herein in its entirety by reference.

BACKGROUND OF THE INVENTION

1. The Field of the Invention

The present invention relates to an improved artificial toe joint. More specifically, the present invention relates to an artificial toe joint providing increased durability and reduced damage to the surrounding bone.

2. State of the Art

Toe joints such as the proximal metatarsal phalangeal joint, the proximal most toe joint of the foot, may become damaged from injury, etc. and may then be replaced. As a toe joint is damaged and deteriorates, symptoms may include loss of propulsion, transfer lesions, metatarsalgia (pain and inflammation of the ball of the foot), gait alterations, pain, etc. Indicators for joint replacement include: hallux limitus, hallux rigidus, hallux abducto valgus, rheumatoid arthritis, osteoarthritis, previous surgery at the joint which is painful or which resulted in an instable joint, joint problems after a prior joint surgery, failed joint surgery, etc.

The interphalangeal joints and other joints of the toes may also become damaged, and it will be appreciated that the artificial joint of the present invention may also be applied to these toe joints as well. Specifically, the present invention can be used in the joints including, but not limited to the inter phalangeal joints of all lesser digits, as well as the metatarsal phalangeal joints of all lesser digits. It is appreciated that the fusion of these joints does not result in the same loss of mobility and the same degree of detriment to a patient as does the fusion of the proximal metatarsal phalangeal joint, but does result in some detrimental effects for the patient. For example, the second metatarsal phalangeal joint can develop Freiberg's infraction resulting in metatarsal head deformation and loss of cartilage. The treatments are generally limited following Freiberg's.

Furthermore, the invention is not restricted to the metatarsal phalangeal joint of the first digit and can be utilized to replace the inter-phalangeal joint of the first digit which too is often damaged secondary to cartilage loss and is often fused. As will be explained below, the present invention is suitable for both conditions as it allows resurfacing of the joint.

Currently, artificial metatarsal joints exist which are implanted by cutting off the ends of the bones which form the natural joint (typically the metatarsal phalangeal joint), reaming out the cut ends of the bones (the base of the proximal phalanx and the head of the metatarsal) to receive the stems of the artificial joint, and inserting the artificial joint. The prior art artificial joints place stress on the bone surrounding the joint, often resulting in destruction of the bone surrounding the joint and thus failure of the artificial joint. It is common for artificial toe joints to fail about five years after replacement. Once the joint has failed, the bone structure surrounding the joint (the cut end and hole into which the artificial joint has been inserted) has often degraded to where the joint must be fused together. It is easily appreciated that a fused toe joint is highly undesirable as it limits mobility, and may make it significantly harder for a person to accomplish daily tasks such as walking.

It is important to note that current joints generally cannot provide compensation for angular deviations at the first metatarsal phalangeal joint. Such deviations include, but are not limited to: hallux abductovalgus, inter phalageous angle, plantarflexed as well as dorsiflexed metatarsal head, inter-metatarsal angles, and proximal articular set angle as well as the distal articular set angle. The advent of a total implant that can compensate for such deviations is very advantageous secondary to angular correction. These corrections will allow reduction of pain proximally in the foot as well as extend the life of the implant.

It is desirable that an artificial toe joint should achieve certain results. The artificial joint should be stable and provide stability to the patient, such as when standing and walking. The artificial joint should provide a pain free range of motion to the patient. The artificial joint should allow the patient to walk and move in a natural manner. It is desirable that installation of an artificial joint provide an increase in activity levels and an improvement in the lifestyle of the person. An artificial joint should provide long term success; promoting the strength of the surrounding bone and resisting deterioration of the resulting joint so as to minimize the need for the later fusing of the joint.

There is thus a need for an artificial toe joint which overcomes the limitations of available artificial toe joints. Specifically, there is a need for an artificial toe joint which has less affect on the bone structure around the joint. It is also desirable to provide an artificial joint which allows for angular deviation correction to reduce stress and strain proximally in the foot. It is also desirable to provide resurfacing of the existing anatomy which is low profile and anatomically similar to existing structures. Thus, there is a need for an artificial toe joint which provides greater long term success of the artificial joint and which replicates existing anatomical motion. There is also a need for an artificial toe joint which may be used in replacing a previously installed artificial toe joint which has failed to thereby eliminate the need to fuse the joint. There is a further need for an artificial toe joint which is easier to install. It will be appreciated that achieving any one of these will be an improvement in artificial toe joints, while achieving multiple of these ends would constitute a substantial improvement for patients.

SUMMARY OF THE INVENTION

It is an object of the present invention to provide an improved artificial toe joint.

According to one aspect of the invention, an improved artificial toe joint is provided. More specifically, the joint of the present invention is particularly suited for a first metatarsal phalangeal joint replacement, but may be used for other toe joints as well. Ideally, artificial joints made according to the present invention can be used for the interphalangeal joints of the first digit, the interphalangeal joints of the lesser digits, as well as the metatarsal phalangeal joints of the lesser digits.

According to one aspect of the present invention, an artificial toe joint is provided which encases the ends of the bones adjacent the joint. By enclosing the ends of the bones adjacent the joint, the artificial joint results in a more stable structure and reduces the stress on the ends of the bone by distributing the stresses along the bone, promoting improved long term success for the artificial joint.

In accordance with another aspect of the present invention, a resurfacing technique is provided which is unlike any other on the current market. This resurfacing is accomplished through the advent of a low profile joint that contours the existing anatomical structures providing minimal bony disruption, placing the articular surface in alignment thus reducing any existing angular deviations, providing anatomical motion, and reducing pain. In addition it is important to note that current joints generally can not compensate for metatarsal length variations. The present invention may include a flexible articulating surface that can be varied in width to compensate for first ray length. When such variances are considered and addressed the resultant mobile and rectus first ray will provide for pain reduction both distally and proximally to the implanted surface.

According to another aspect of the present invention, enclosing the ends of the bone surrounding the artificial joint may allow the present artificial toe joint to be installed in place of previously installed artificial toe joints which have failed. Such an installation may eliminate the need to fuse the joint. Additionally, the artificial joint of the present invention makes possible the modification of existing fused joints.

These and other aspects of the present invention are realized in an artificial joint as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single Figure, and as such, multiple figures are presented to separately illustrate the various details of the invention in greater clarity.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
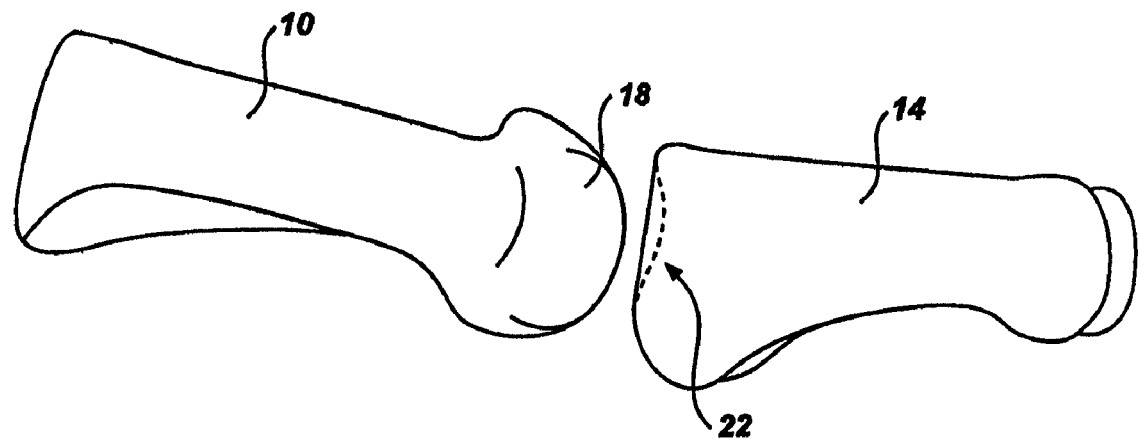
FIG. 1 shows a perspective view of a first metatarsal bone and a proximal phalangeal bone which comprise the first metatarsal phalangeal toe joint.

Turning now to FIG. 1, a perspective view of the bones of the proximal toe joint (the metatarsal phalangeal joint) is shown. The innermost toe joint (closest to the foot) is shown. The joint includes a metatarsal bone 10 and a phalange bone 14. The metatarsal bone 10 includes a rounded end 18 which, together with a depression 22 in the phalange bone 14 and the associated cartilage and tissue, forms the joint. The replacement of the toe joint may be necessitated by damage to the bones 10, 14 or to the cartilage and tissues of the joint. (While described in context of the first metatarsal phalangeal joint, the same anatomical presentations exist throughout the lesser metatarsal phalangeal joints with the exception of size. Additionally, the inter-phalangeal joints also mirror somewhat the metatarsal phalangeal joints.)

Figure 2:
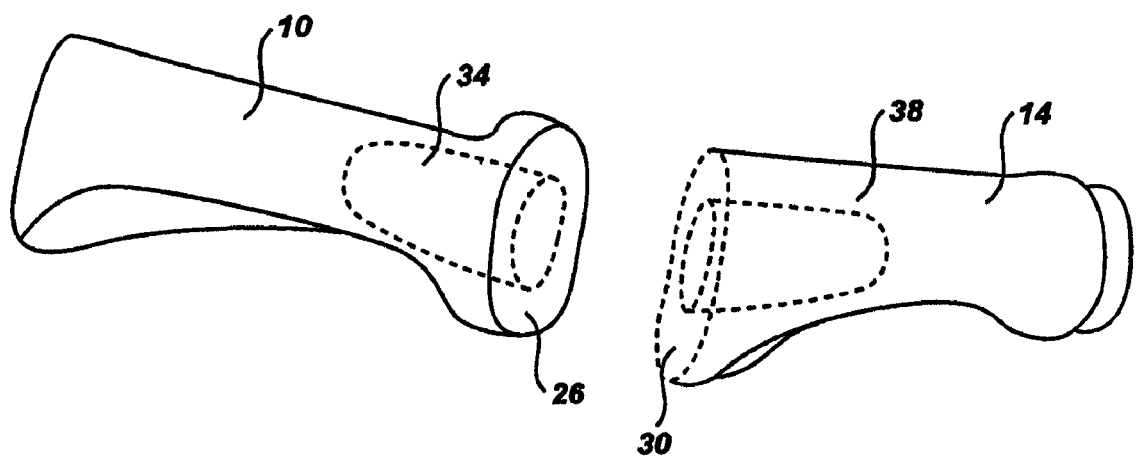
FIG. 2 shows the toe joint of FIG. 1 cut to receive a prior art artificial joint.

FIG. 2 shows the bones 10, 14 of FIG. 1. The bones 10, 14 have been prepared for an artificial toe joint of the prior art. The ends of the bones 10, 14 have been cut flat as indicated at 26, 30. Additionally, holes 34, 38 have been formed in the ends of the bones 10, 14 to receive the artificial toe joint. The artificial joint has posts on both ends which are fused into the holes 34, 38 to attach the joint to the bones 10, 14. A flexible member, not shown, connects the posts to form the artificial toe joint and to allow movement of the phalange bone 14 relative to the metatarsal bone 10.

A problem with the prior art artificial joints is that the strength and structure of the bone is compromised by the artificial joint. The toe bones 10, 14 are fairly small, and their strength may be significantly compromised by drilling out the bones. The posts of the artificial joint combined with the hollowed out bones 10, 14 result in places of high stress and typically result in damage to the bones. Once the bone is damaged, it may be difficult to repair the damage and install another artificial joint. Thus, once an artificial joint fails, the bones 10, 14 must often be fused together.

Figure 3:
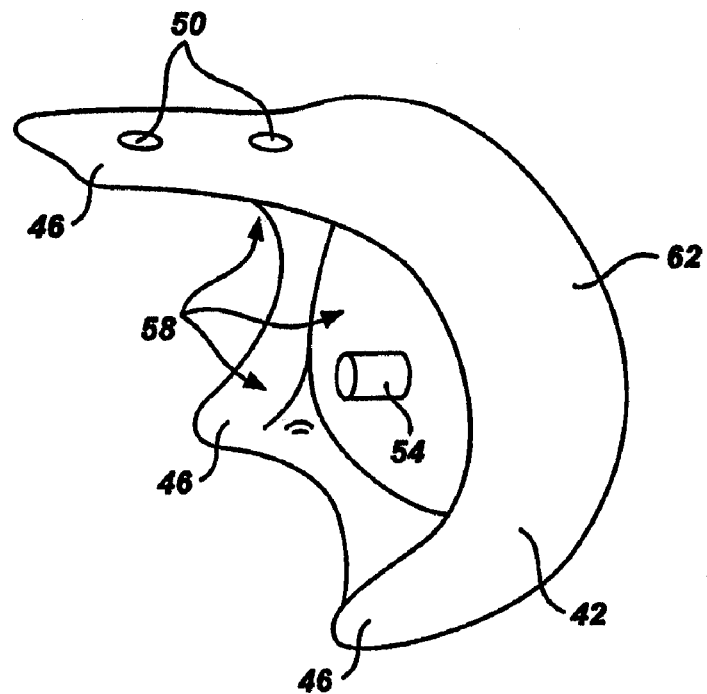
FIG. 3 shows a perspective view of the back side of one piece of an artificial joint of the present invention.

FIG. 3 shows a perspective view of the back side of an artificial joint piece of the present invention. The artificial joint member 42 shown replaces the rounded end 18 of the metatarsal bone 10. The artificial joint member 42 is attached to the exterior of the bone 10 by providing appendages which extend around the bone, such as arms 46. One or more of the arms 46 may include holes 50 for receiving a pin or screw to further secure the artificial joint member 42 to the bone.

The process for placing the artificial toe joint will typically include the use of a pre-formed template system. The template will be placed intra articular and serve as a guide for shaping the head of the metatarsal as well as the base of the proximal phalanx. The template will serve as a guide for placement of the sagital saw blade, thus reducing surgical error and allowing for ease of placement of the joint. The template will cause the corresponding bony surface to mirror the inside of the articulated resurfacing implant. The template system will vary in size to compensate for variance in bony girth. The template used will correlate numerically with the implant that will be placed, thus improving surgical success as well as implant longevity.

While the bones may be predrilled to receive posts in the artificial joint, it is believed that pre-drilling is not required, as the posts can be tapped into the bone with a mallet. The posts may vary in length, but remain relatively small to facilitate placement and securing of the implant.

A flexible member, discussed in more detail below, may be placed after the implant has been positioned. Once in place, the length of the first ray will be determined using removable and reusable guides. Once the width and type of flexible member has been determined, the actual flexible disk can be opened and placed on the metatarsal side of the joint. This will be placed using a tongue and groove system that can be modified. Following placement, the first digit can be placed through range of motion to ensure correction and placement suitability.

It has been found that it is preferable for the template system to produce a mirrored surface on the metatarsal (etc.) head to that of the implant. This can be done with minimal bone reconstruction and with the use of the previously described template system. Thus, the implant essentially becomes a resurfaced metatarsal head, functioning in the same manner as the original prior to damage.

The artificial joint member 42 may also include a small post or spike 54 to aid in securing the artificial joint member to the bone. The post or spike 54 is typically small compared to the size of the bone and does not compromise the strength of the bone. The post or spike 54 can help keep the artificial joint member 42 from sliding back and forth across the front of the bone.

The inside surfaces of the artificial joint member 42, as indicated at 58, may be made somewhat rough or porous, and may be coated with compounds which promote the adhesion of the bone to the artificial joint member. These compounds may be bone growth compounds. The artificial joint member 42 may thus be initially held in place by the post or spike 42 and pins or screws, and then may become further attached to the bone as the bone grows and affixes itself to the inside surface 58 of the artificial joint member.

Figure 5:
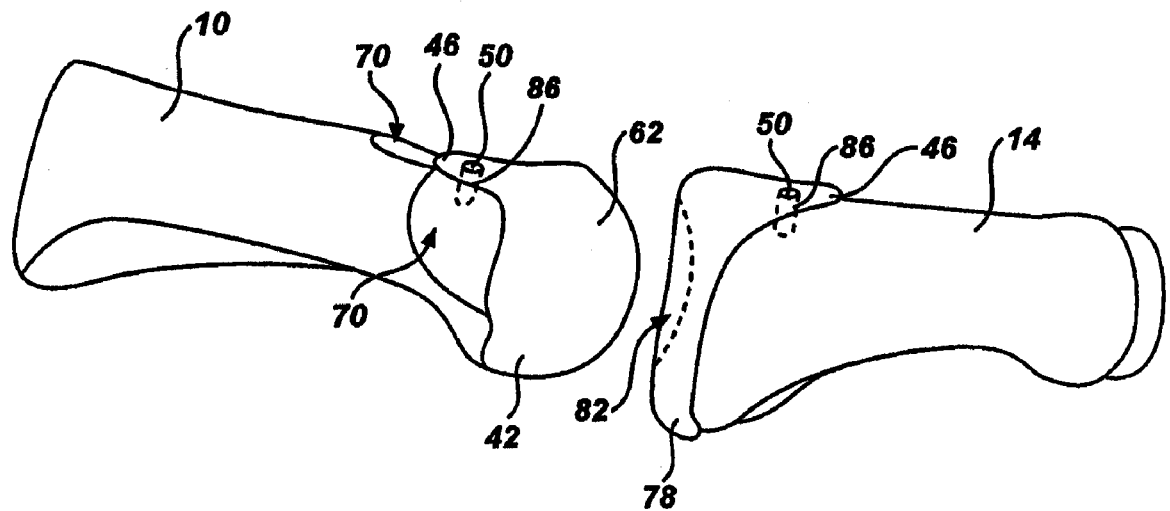
FIG. 5 shows the toe joint of FIG. 1 having the present artificial joint installed thereon.
Figure 6:
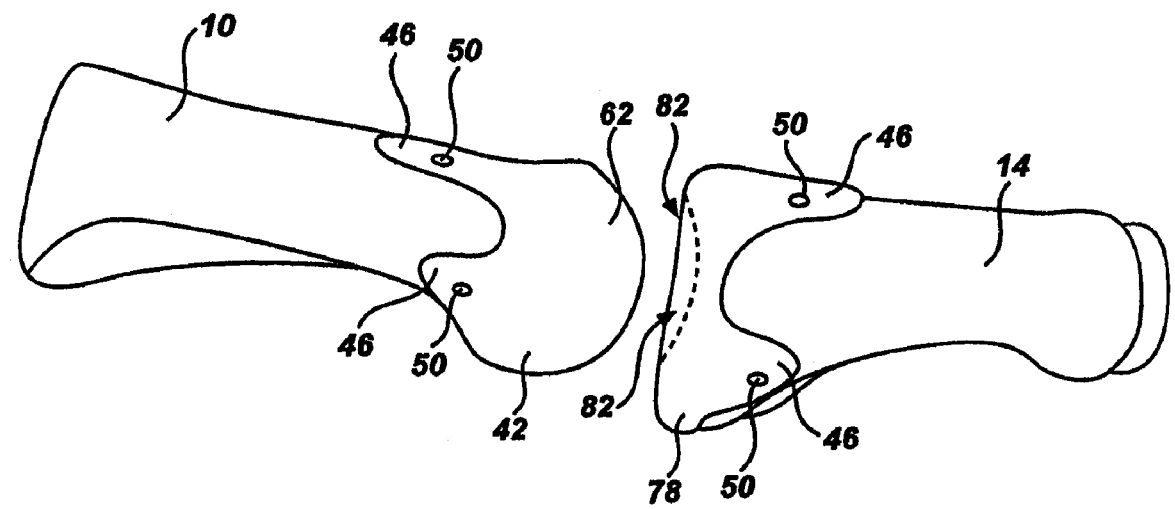
FIG. 6 shows another view of the toe joint of FIG. 1 having an artificial joint of the present invention installed thereon.
Figure 7:
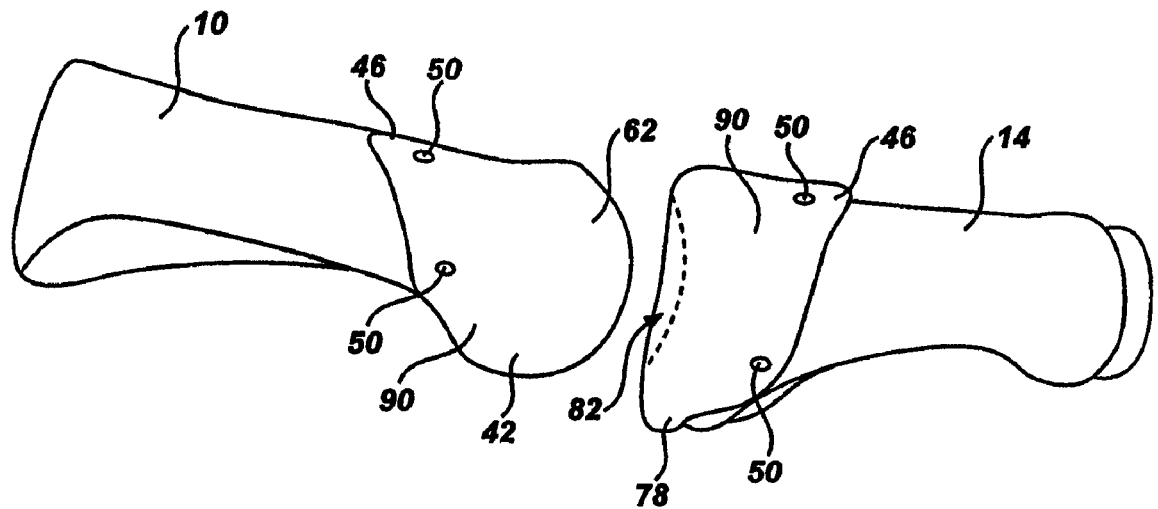
FIG. 7 shows another view of the toe joint of FIG. 1 having the present artificial joint installed thereon.

The artificial joint is formed by the first artificial joint member 42 and a second artificial joint member (78 of FIGS. 5-7). The back side of artificial joint member 78 (which is attached to bone 14) is similar to that of artificial bone member 42, having arms 46 or the like for attachment to the sides of the bone 14, a post or spike 54, holes 50 for pins or screws, a compound for promoting adhesion to the bone, etc. Artificial joint member 42 is formed with a rounded end 62, similar to the rounded end 18 of bone 10. Artificial joint member 78 is formed with a recess similar to the recess 22 of bone 14. Thus, the artificial joint recreates the natural joint, promoting a natural motion and use of the joint.

Like the inside surfaces of the artificial joint member, the arms 46 may be coated with material, such as bone morphogenic protein, to facilitate attachment to the bone. In a preferred embodiment, the dorsal arm 46 may be porous and coated on both inside and outside surfaces with bone growth enhancing material.

Figure 4:
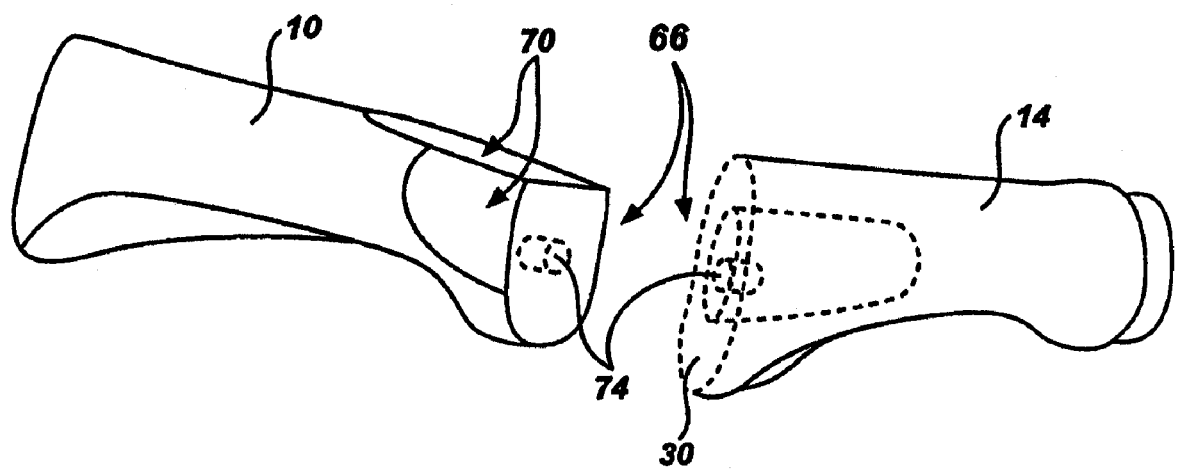
FIG. 4 shows the toe joint of FIG. 1 cut to receive the artificial joint of the present invention.

FIG. 4 shows the toe bones 10, 14 of FIG. 1 as having been cut and prepared for an artificial joint of the present invention. The adjoining ends of the bones 10, 14 have been cut off as indicated at 66. Additionally, the top, bottom, or sides of the bones 10, 14 may be cut as indicated at 70 to provide sufficient room for the artificial joint member and to create sufficient attachment surfaces for the same. Additionally, a small hole or recess 74 may be formed in the ends of the bone 10, 14 to receive any post or spike (54 of FIG. 3) which may be utilized in the artificial joint members. It will be appreciated that the hole 74 may not be necessary if the post or spike 54 is not used, or is small enough and appropriately shaped to be simply pressed into the bone 10, 14. (It will be appreciated that other processes of bone preparation may be used as will be explained below).

FIG. 5 shows the first and second artificial joint members 42, 78 of the present invention attached to the toe bones 10, 14. The rounded end 62 disposed on the front or first side of the artificial joint member 42 is similar in shape and size as the end 18 of the natural bone 10. The arm 46 (or a collar, etc.), extending from the back or second side holds the rounded end securely to the bone.

Artificial joint member 78 is formed with a recess 82 in the front or first side which is generally rounded and concave to receive the rounded end 62, and to be similar in shape and function to the recess 22 found naturally in bone 14. Arm 46 (or a collar, etc.) extends from the back or second side to hold the second artificial toe joint member 78 to the bone.

Pins or screws 86 may be inserted through the holes 50 in the artificial joint members 42, 78 and into the bones 10, 14 to secure the artificial joint members. As has been discussed, the insides of the artificial joint members may be formed with a texture or coated with a bone growth promoter to stimulate the bones 10, 14 to adhere to the artificial joint members.

FIG. 6 shows an alternate configuration of the artificial joint of the present invention. The artificial joint members 42, 78 are similar to those of FIG. 5 but include additional arms 46. FIG. 5 shows one larger arm 46 at the top of the artificial joint members 43, 78. FIG. 6 shows additional arms 46 on the sides of the artificial joint members 42, 78, and may include additional holes 50 for pins or screws to secure the artificial joint members to the bones 10, 14. Other attachment means could also be used. The artificial joint members 42, 78 may also contain the other structures discussed with respect to FIGS. 3-5 which are not shown here for clarity.

FIG. 7 similarly shows an alternate configuration of an artificial joint of the present invention. The artificial joint members 42, 78 are formed with elongated side walls 90 which extend around a much larger portion of the bones 10, 14; such as extending around the tops and sides of the bones. The side walls 90 may form a collar which wraps around the end of the bone 10, 14. The artificial joint members 42, 78 may also be formed with arms 46 which extend farther than the side walls 90, and may include one or more holes 50 for receiving pins or screws to affix the artificial joint members to the bone 10, 14. The artificial joint members 42, 78 also include the remaining structures shown in FIGS. 3-6 but which are not shown for clarity.

In viewing FIGS. 5-7, it can be appreciated that the number and relative size of arms 46 may be varied. Additionally, the use of side walls 90 which extend around a more substantial portion of the bones 10, 14 may be varied. Providing more arms or longer arms, or using side walls 90 may make the artificial joint members 42, 78 more difficult to install, or make each particular size of artificial joint member fit a more limited size of toe bones 10, 14. However, providing more or larger arms 46 or wide walls 90 may achieve a stronger bond to the bones 10, 14 and result in a stronger artificial joint which may be more durable and last longer.

Additionally, it may be possible to repair damaged bones 10, 14 by using more arms 46 or side walls 90. As has been mentioned, installation of prior art artificial joints may result in bone damage, either degradation of the interior of the bone or cracking or breaking of the bone, etc. The present invention provides artificial joint members which may be used to cover the damaged part of the bone and extend back to undamaged bone, and thereby provide an alternative to simply fusing the bones together. Additionally, some injuries to the joint and surrounding bones 10, 14 may break or crack the bones in a manner which prevents installation of a prior art artificial joint, such as where cracks or breaks do not leave sufficient strength in the bone for drilling out the bone and installing a prior art artificial joint.

The artificial joint of the present invention is thus advantageous for several reasons. The artificial joint does not require that the bones be drilled out for installation, and as such does not compromise the strength of the bone and result in high stresses in the area of the artificial joint. This may typically result in an artificial joint which is stronger and which lasts longer than the prior art artificial joints. Additionally, because it extends around the exterior of the bones, the artificial joint of the present invention may be used in some cases to provide an artificial joint where bone damage may otherwise prevent installation of an artificial joint. Thus, the present joint may be installed when another artificial joint must be removed. The artificial joint members may be made to extend past the damaged bone and be connected to strong bone.

The present artificial joint is also advantageous as it better disperses energy through the bones by attachment to the harder outer surface of the bone and not the generally softer inner surface of the bone. The artificial joint also provides ease of surgical placement, as the prior art artificial joints require the proper alignment and drilling of a hole into the bone, where the inventive artificial joint is attached to and aligned by the exterior of the bone.

In addition to the above, the artificial toe joint of the present invention also provides the ability to correct angular deviations, first ray length, as well as providing a resurfacing technique for damaged bones in the toe. Each of these individually provides an improved artificial toe joint and collectively provide a substantial improvement in both technique and ultimate function of the joint.

Figure 8A:
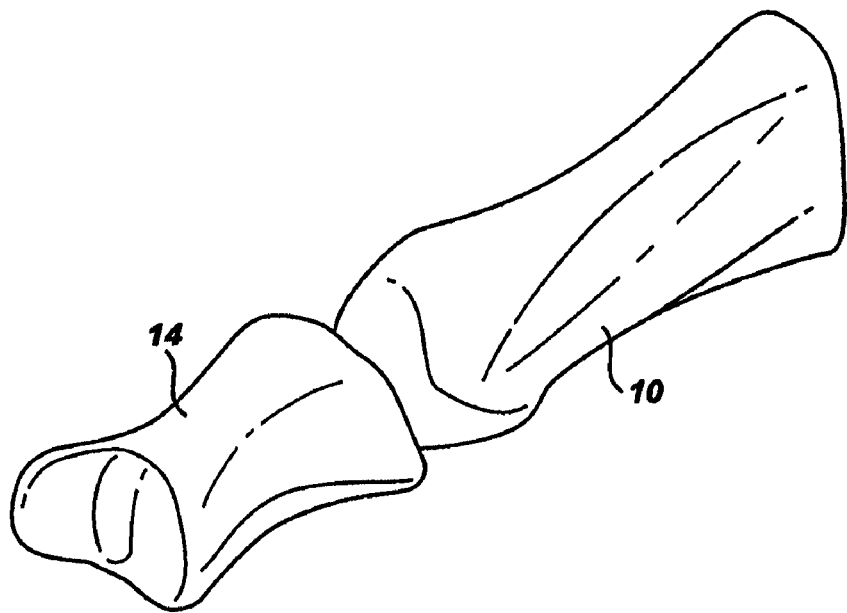
FIG. 8A shows a perspective view of a metatarsal bone and proximal phalanx bone forming a toe joint.
Figure 8B:
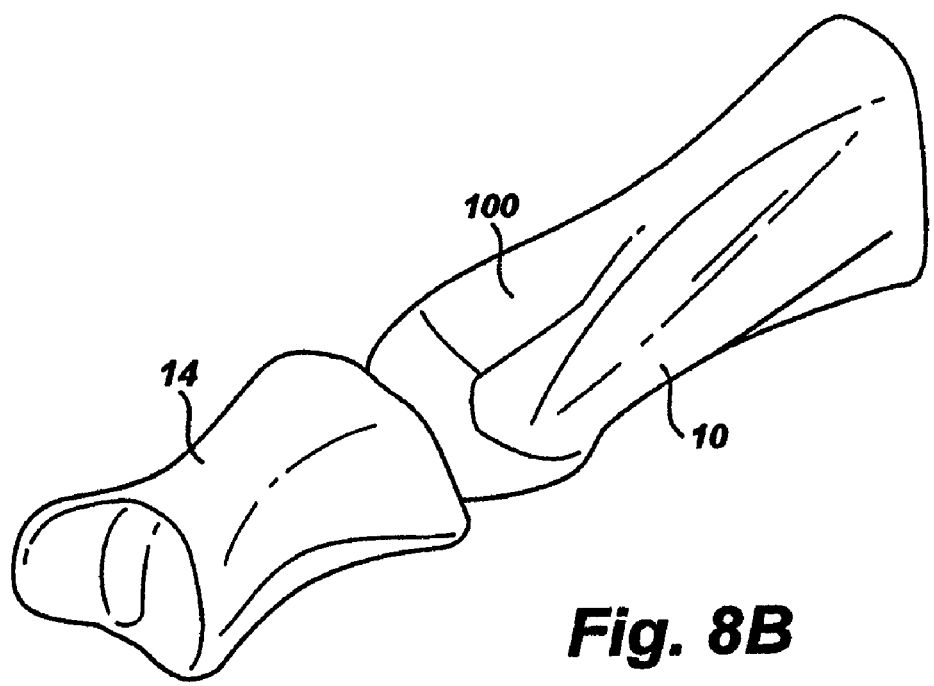
FIG. 8B shows the bones shown in FIG. 8A having a dorsal cut formed on the metatarsal bone.
Figure 8C:
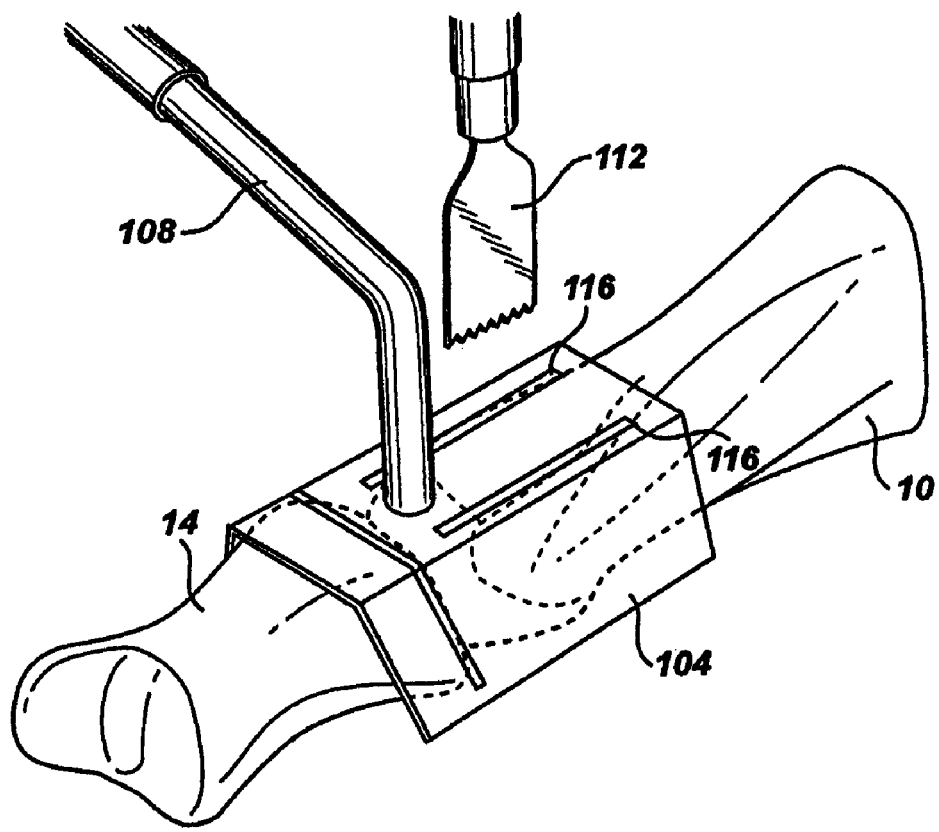
FIG. 8C shows the toe joint of FIGS. 8A and 8B and a template used for making cuts on the toe joint.

Turning now to FIGS. 8A through 8C, there is shown the process for preparing metatarsal bone and proximal phalanx bone for installation of a joint made in accordance with the present invention. FIG. 8A shows a perspective view of the metatarsal bone 10 and the proximal phalanx 14. As mentioned regarding FIG. 1, the end of the metatarsal bone is generally convex, while the adjacent end of the proximal phalanx is somewhat concave.

The first step in the process is generally to make a dorsal cut, as indicated at 100 in FIG. 8B. The dorsal cut can provide both a surface for ultimate use by the implant, as well as a point of reference for use by a template 104, as shown in FIG. 8C. The template 104 is placed on the metatarsal bone 10 and held in place by a handle 108. An oscillating blade 112 is then advanced through holes 116 in the template 104 to shape the sides of the metatarsal bone.

Figure 9:
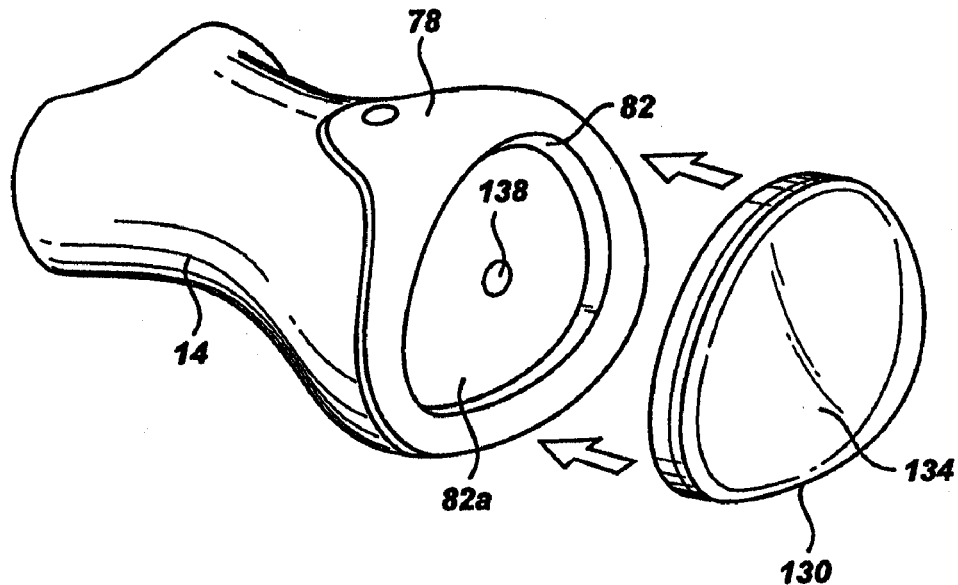
FIG. 9 shows a proximal phalanx bone artificial joint member and an implant in accordance with one aspect of the present invention.

FIG. 9 shows an exploded view of the proximal phalanx bone with an implant (artificial joint member 78) disposed thereon. As was mentioned previously, the artificial joint member will generally have a recess 82. The recess 82 may receive the convex surface of the implant on the metatarsal bone directly, or a cushion or insert 130, may be disposed between the two. If desired, the insert 130 can be provided with structure which assists in alignment of the implants of the artificial joint. More specifically, the insert 130 may include a concave face 134 configured to receive the convex rounded end 62 of the implant 42 (FIG. 5).

The insert 130 may be made from a variety of biocompatible materials, such as silicone, certain foams, plastics, etc. Additionally, it is preferred that the insert be flexible, both to provide some cushioning and to facilitate placement in the artificial joint member 78 as explained below.

The artificial joint member 78 may also include a generally flat bottomed recess 82a with a detent 138 formed therein. The recess 82a and detent 138 can help hold the insert 130 in place, thereby providing cushioning in the joint. The insert 130 also provides the advantage that different thicknesses of inserts can be used to adjust for metatarsal length variations. Thus, not only is the doctor able to create an artificial toe joint which more closely matches the normal anatomical structure, he or she can ensure the proper spacing between the metatarsal and proximal phalanx.

Figure 9A:
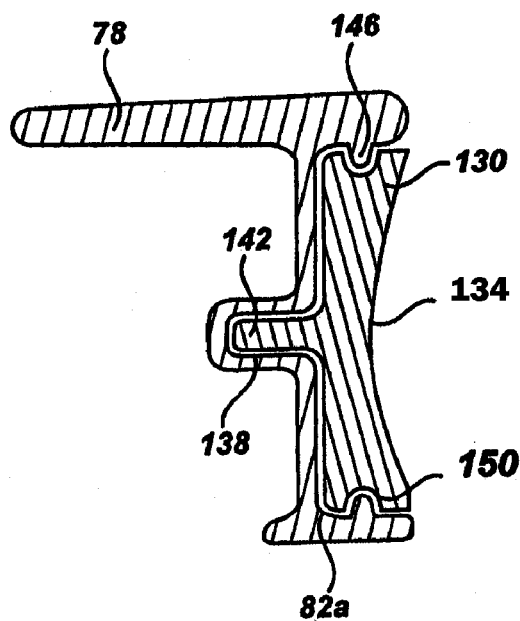
FIG. 9A shows a cross-sectional view of the artificial joint member and implant of FIG. 9.

FIG. 9A shows a cross-sectional view of the artificial joint member 78, and the insert 130. The insert 130 may include a projection 142 disposed opposite the concave face 134 to help seat the insert in the recess 82a of the artificial joint member 78. Additionally, the recess 82a may include a generally annular rib 146 which is designed to project into a generally annular groove 150 in the side of the insert 130. (It will be appreciated that the annular rib 146 could be replaced with a projection and the annular groove 150 with a detent or other similar structures and FIG. 9A can be interpreted to show such structures.) This helps to hold the insert 130 in place and leaves a proximal phalanx with an end which more closely resembles the original anatomical structure.

Figure 10A:
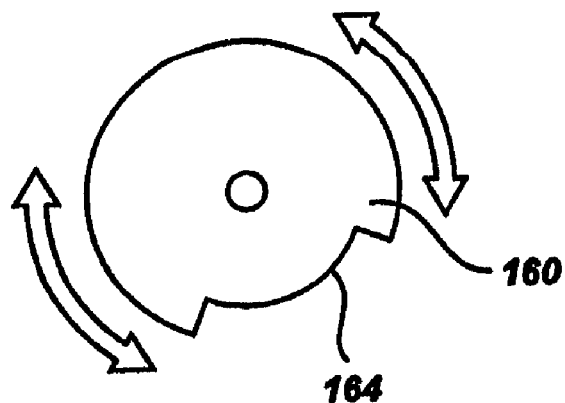
FIG. 10A shows a bit used for implant surface preparation.

FIG. 10A shows a bit 160 which can be used to improve implant surface preparation. Rather than using the template system described in FIGS. 8A-8C, the bit 160 is attached to a drill (not shown). The bit 160 is a concave oscillating bit and includes a notch 164 for the sesmoids.

Figure 10B:
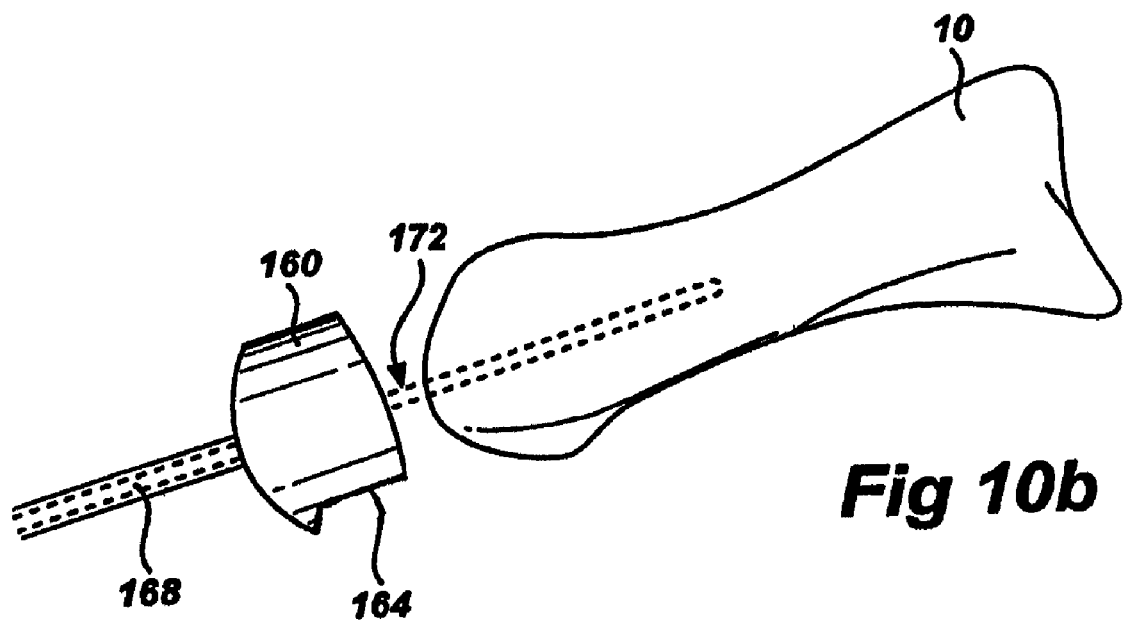
FIGS. 10B and 10C show side views of the preparation of the metatarsal and proximal phalanx using the bit of FIG. 10A.
Figure 10C:
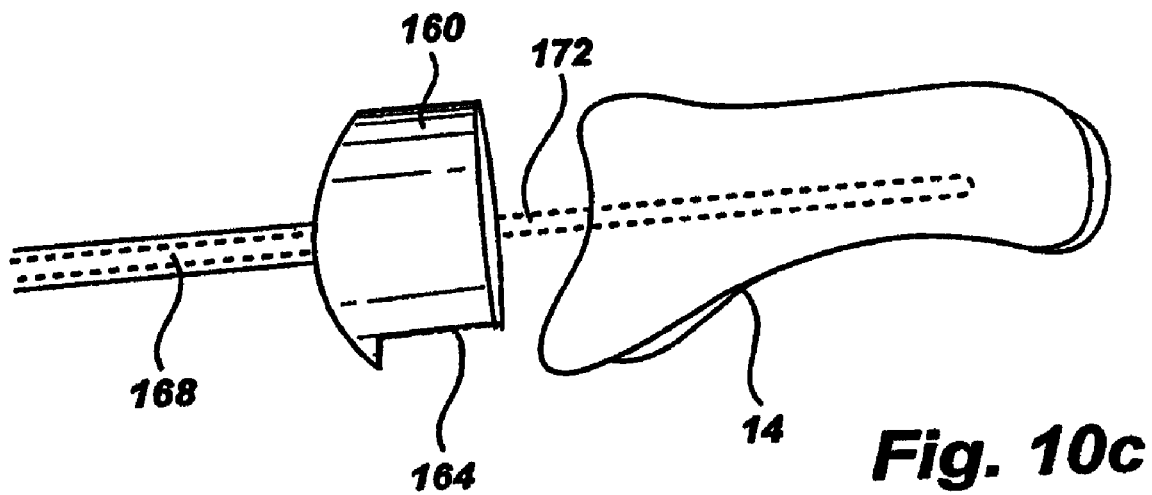

Preferably the drill includes a cannulated shaft 168 with a K-wire 172 extending therefrom. The K-wire is used to align the bit 160 on either the metatarsal or proximal phalanx depending which piece is being worked. Thus, FIG. 10B shows the bit 160 being advanced on the metatarsal, and FIG. 10C shows the bit being advanced on the proximal phalanx.

The bit 160 allows the ends of the respective bones to be reshaped for improved mounting of the artificial joint members and allows a remaining bone structure which is more anatomically correct. Once the bit 160 has prepared the bones, the artificial joint members can be attached, thereby creating a new joint.

Because the artificial joint engages a much greater surface area of the bones, less stress is placed on the bones and the risk of further damage is decreased. Additionally, if the insert 130 were to fail for some reason, it can simply be replaced without further damage to the bones. This is in sharp contrast to the artificial toe joints of the present invention which generally result in fusion of the bones when they fail.

There is thus disclosed an improved artificial toe joint. It will be appreciated that numerous changes may be made to the present invention without departing from the scope of the claims.

What is claimed is:

1. An artificial toe joint comprising:
    an artificial metatarsal joint member sized for attachment to the distal end of a metatarsal bone, the artificial metatarsal joint member having a first side and a second side, the first side being convex and generally hemispherical, the artificial metatarsal joint member having an appendage forming an attachment member extending from a lateral edge of the artificial metatarsal joint member in a direction generally opposite the first side; and
    an artificial phalangeal joint member, sized for attachment to a phalangeal bone, and having a first side and a second side, the first side having a portion which is generally concave and having a generally complementary surface for receiving at least a portion of the first side of the artificial metatarsal member and an attachment member extending from a lateral edge of the artificial phalangeal member in a direction generally opposite from the first side of the artificial phalangeal joint member, such that when the first side of the artificial metatarsal joint member and the first side of the artificial phalangeal joint member are brought into complementary engagement, the attachment member of the artificial metatarsal member and the attachment member of the artificial phalangeal member extend away from the engagement in generally opposite directions; and a fastener extendable through one attachment member for securing the attachment member to an exterior surface of a bone.

2. The artificial joint of claim 1, wherein one of the attachment members extends from a position at the top of the artificial metatarsal joint member and the other extends from a position at the top of the artificial phalangeal joint member such that when installed, the attachment members, extend along the top of the phalange bone and metatarsal bone, respectively, and the first sides of the artificial metatarsal joint member and artificial phalangeal joint member engage one another to form a joint.

3. The artificial joint of claim 2, wherein the attachment member on the artificial phalangeal joint member comprises a collar such that when the artificial phalangeal joint member is disposed with the second side mounted on a proximal end of a phalangeal bone, the collar extends along top and lateral sides of the phalangeal bone.

4. The artificial joint of claim 2, wherein the attachment member comprises at least one arm.

5. The artificial joint of claim 1 wherein both the artificial metatarsal joint member and the artificial phalangeal joint member have fasteners extending through the attachment members to secure the attachment members to the exterior of the bones.

6. An artificial toe joint comprising:
a first artificial joint member having a first side and a second side and being configured for attachment to a metatarsal bone;
a second artificial joint member having a first side and a second side and being configured for attachment to a phalange bone; and
wherein the first side of the first artificial joint member and the first side of the second artificial joint member comprise generally complementary surfaces disposed adjacent to one another to form a movable joint; and wherein the second side of the first artificial joint member and the second side of the second artificial joint member are configured for attachment to the bones forming the movable joint which is to be replaced; the second sides of the first artificial joint member and second artificial joint member each having a structure extending peripherally from the respective artificial joint member and away from the generally complementary surfaces to form attachment members configured for extending along exterior portions of bones that form the joint being replaced; and
wherein the attachment members on the second side of the first artificial joint member and the second side of the second artificial joint member comprise arms, one of said arms being for attachment to a metatarsal bone and one of said arms being for attachment to a phalange bone; and
wherein the attachment members comprise at least one second arm on one of the first artificial joint member and second artificial joint member, such that arms are attached along the top and side of at least one of the metatarsal and phalange bones.

7. The artificial joint of claim 6, wherein the arms are configured to be attachment to the metatarsal and phalangeal bones along the tops of the metatarsal and phalange bones.

8. The artificial joint of claim 6, wherein the first artificial joint member and second artificial joint member comprise side walls which are configured to extend around tops and sides of the metatarsal and phalange bones.

9. The artificial joint of claim 6, wherein the second side of the first artificial joint member and the second side of the second artificial joint member comprise receptacles for receiving the ends of the bones.

10. The artificial joint of claim 9, wherein the second side of the first artificial joint member and the second side of the second artificial joint member comprise a small post or spike located in the receptacle and configured for engaging the ends of the bones.

11. An artificial toe joint comprising:
a first artificial joint member having a first side and a second side and being configured for attachment to a metatarsal bone;
a second artificial joint member having a first side and a second side and being configured for attachment to a phalange bone;
wherein the first side of the first artificial joint member and the first side of the second artificial joint member comprise generally complementary surfaces disposed adjacent to one another to form a movable joint; and wherein the second side of the first artificial joint member and the second side of the second artificial joint member are configured for attachment to the bones forming the movable joint which is to be replaced; the second sides of the first artificial joint member and second artificial joint member each having a structure extending peripherally from the respective artificial joint member and away from the generally complementary surfaces to form attachment members configured for extending along exterior portions of bones that form the joint being replaced;
wherein the attachment members on the second side of the first artificial joint member and the second side of the second artificial joint member comprise arms, one of said arms being for attachment to a metatarsal bone and one of said arms being for attachment to a phalange bone; and
wherein the arms comprise holes formed therein and further comprising a pin or screw for attaching the first and second artificial joint members to the bones.

12. An artificial toe joint comprising:
an artificial metatarsal joint member sized for attachment to the distal end of a metatarsal bone, the artificial metatarsal joint member having a first side and a second side, the first side being convex and generally hemispherical, the artificial metatarsal joint member having an appendage forming an attachment member extending from a lateral edge of the artificial metatarsal joint member in a direction generally opposite the first side; and
an artificial phalangeal joint member, sized for attachment to a phalangeal bone, and having a first side and a second side, the first side having a portion which is generally concave and having a generally complementary surface for receiving at least a portion of the first side of the artificial metatarsal member and an attachment member extending from a lateral edge of the artificial phalangeal member in a direction generally opposite from the first side of the artificial phalangeal joint member, such that when the first side of the artificial metatarsal joint member and the first side of the artificial phalangeal joint member are brought into complementary engagement, the attachment member of the artificial metatarsal member and the attachment member of the artificial phalangeal member extend away from the engagement in generally opposite directions; and wherein the first side of the artificial phalangeal joint member comprises a recess configured for receiving an insert.

13. The artificial joint of claim 12, wherein the artificial phalangeal joint member further comprises an insert configured for disposition in the recess to engage the artificial metatarsal joint member, the insert forming the generally complementary surface of the artificial phalangeal joint member.

14. The artificial joint of claim 13, wherein the first side of the artificial phalangeal joint member comprises a retaining member configured to hold the insert in the recess.

15. The artificial joint of claim 14, wherein the retaining member comprises a detent in the artificial phalangeal joint member configured for receiving a projection on the insert.

16. The artificial joint of claim 15, wherein the retaining member comprises a generally annular rib configured to nest in a generally annular groove on the insert.

17. An artificial toe joint comprising:
a first artificial toe joint member having a first side and a second side;
a second artificial toe joint member having a first side and a second side; and
wherein the first side of the first artificial toe joint member and the first side of the second artificial toe joint member comprise generally complementary arcuate surfaces, the first side of one of said first artificial joint member and second artificial joint member being generally concave and the first side of the other of the first artificial joint member and second artificial joint member being generally convex, the first sides disposed adjacent one another to form a movable ball in socket toe joint; and
wherein the second side of the first artificial toe joint member and the second side of the second artificial toe joint member are generally concave, each being configured to receive an end of a respective bone of a toe joint so as to cover an end of the bone, and wherein at least a portion of the second side of the first artificial joint member and a portion of the second side of the second artificial joint member extend away from the first side of the first artificial joint member and the first side of the second artificial joint member, respectively, so as to extend along an exterior portion of the respective bone remote from the end and are configured for attachment to the bones forming the joint; and
wherein the second artificial joint member comprises an insert disposed in the first side thereof, the insert having a concave surface, and wherein the first artificial joint member has a convex surface for engaging the concave surface of the insert.

18. The artificial joint of claim 17, further comprising a post extending away from the first side of the first artificial toe joint member for insertion into a cavity within a bone.

19. The artificial joint of claim 17, wherein the second side of the first artificial toe joint member is configured for attachment to a metatarsal bone and the second side of the second artificial toe joint member is configured for attachment to a phalange bone.

20. The artificial joint of claim 19, wherein the second side of the first artificial toe joint member and the second side of the second artificial toe joint member comprise arms extending away from the first sides so as to define a portion of the concave second sides, the arms being configured for attachment to the metatarsal and phalange bones.

21. The artificial joint of claim 20, wherein the arms have a porous inner surface and are sized and shaped for attachment to the tops of the metatarsal and phalange bones.

22. An artificial joint comprising:
a first artificial toe joint member sized for attachment to the end of a bone forming a toe joint, the first artificial toe joint member having a first side which is generally hemispherical and a second side, the second side being generally concave and having at least one attachment member extending away from the first side, the at least one attachment member extending so that when the end of a toe bone is disposed in the generally concave second side, the at least one attachment member extends along at least one of the top and side of the toe bone; and
a second artificial toe joint member sized for attachment to the end of a toe bone, the second artificial toe joint member having a first side with a recess formed therein, the recess being generally concave and complementary to the generally hemispherical first side of the first artificial toe joint member, and a second, generally concave side for receiving the end of a second toe bone, the second side having at least one attachment member extending away from the first side and sized to extend along at least one of the top and sides of the second toe bone when the end is disposed in the generally concave second side, the second artificial toe joint member comprising an insert and a recess in the first side for receiving and holding the insert.

23. The toe joint of claim 22, wherein the second artificial toe joint member has an annular rib extending into the recess for engaging and selectively holding the insert in the recess.

24. The toe joint of claim 23, wherein the recess is generally round.

* * * * *